United States Patent [19]
Chin

[11] Patent Number: 5,980,503
[45] Date of Patent: Nov. 9, 1999

[54] ENDOSCOPIC CARDIOPLEGIA INFUSION CANNULA AND METHOD OF USE

[75] Inventor: Albert K. Chin, Palo Alto, Calif.

[73] Assignee: Guidant Corporation, Indianapolis, Ind.

[21] Appl. No.: 08/629,042

[22] Filed: Apr. 8, 1996

[51] Int. Cl.[6] .................................................. A61M 31/00
[52] U.S. Cl. ........................... 604/509; 604/507; 604/96; 604/174
[58] Field of Search ................. 604/49, 52–54, 604/96, 174, 175, 264, 280

[56] References Cited

U.S. PATENT DOCUMENTS

| | | |
|---|---|---|
| 4,119,100 | 10/1978 | Rickett . |
| 4,276,874 | 7/1981 | Wolvek et al. . |
| 4,430,076 | 2/1984 | Harris .......................................... 604/96 |
| 4,527,549 | 7/1985 | Gabbay . |
| 4,531,935 | 7/1985 | Berryessa . |
| 4,531,936 | 7/1985 | Gordon . |
| 4,610,661 | 9/1986 | Possis et al. . |
| 4,664,125 | 5/1987 | Pinto . |
| 4,697,574 | 10/1987 | Karcher et al. . |
| 4,705,507 | 11/1987 | Boyles . |
| 4,712,551 | 12/1987 | Rayhanabad . |
| 4,741,328 | 5/1988 | Gabbay . |
| 4,779,611 | 10/1988 | Grooters et al. . |
| 4,785,795 | 11/1988 | Singh . |
| 5,011,469 | 4/1991 | Buckberg et al. . |
| 5,013,296 | 5/1991 | Buckberg et al. . |
| 5,116,305 | 5/1992 | Milder et al. . |
| 5,167,628 | 12/1992 | Boyles . |
| 5,195,942 | 3/1993 | Weil et al. . |
| 5,203,776 | 4/1993 | Durfee . |
| 5,254,097 | 10/1993 | Schock et al. . |
| 5,308,320 | 5/1994 | Safar et al. . |
| 5,312,344 | 5/1994 | Grinfeld et al. . |
| 5,330,451 | 7/1994 | Gabbay ................................... 604/284 |
| 5,425,705 | 6/1995 | Evard et al. . |
| 5,425,708 | 6/1995 | Nasu ......................................... 604/96 |
| 5,433,700 | 7/1995 | Peters . |
| 5,452,733 | 9/1995 | Sterman et al. . |
| 5,458,574 | 10/1995 | Machold et al. . |

*Primary Examiner*—Corrine McDermott
*Attorney, Agent, or Firm*—Fulwider Patton Lee & Utecht, LLP

[57] ABSTRACT

An endoscopic cardioplegic infusion cannula and its method of use is provided for occluding the ascending aorta and infusing cardioplegic fluid into the coronary arteries. A cannula is inserted suprasternally and the distal end of the cannula is inserted into the ascending aorta. An occlusion balloon on the distal end of the cannula is inflated and occludes the ascending aorta. Cardioplegic fluid is infused through the cannula proximal to the occlusion balloon and perfused into the coronary arteries. In order to effect a better seal where the distal end of the cannula is inserted into the ascending aorta, an outer sheath having a flange is advanced over the cannula into contact with the ascending aorta to compress a portion of the ascending aorta between the flange and the occlusion balloon. Cardiopulmonary bypass is effected in a known manner to supply the patient with oxygenated blood. The cannula and its method of use can be used in a closed or open chest procedure. Sternal lifting is used in conjunction with the present invention to create a greater working space over the heart.

37 Claims, 5 Drawing Sheets

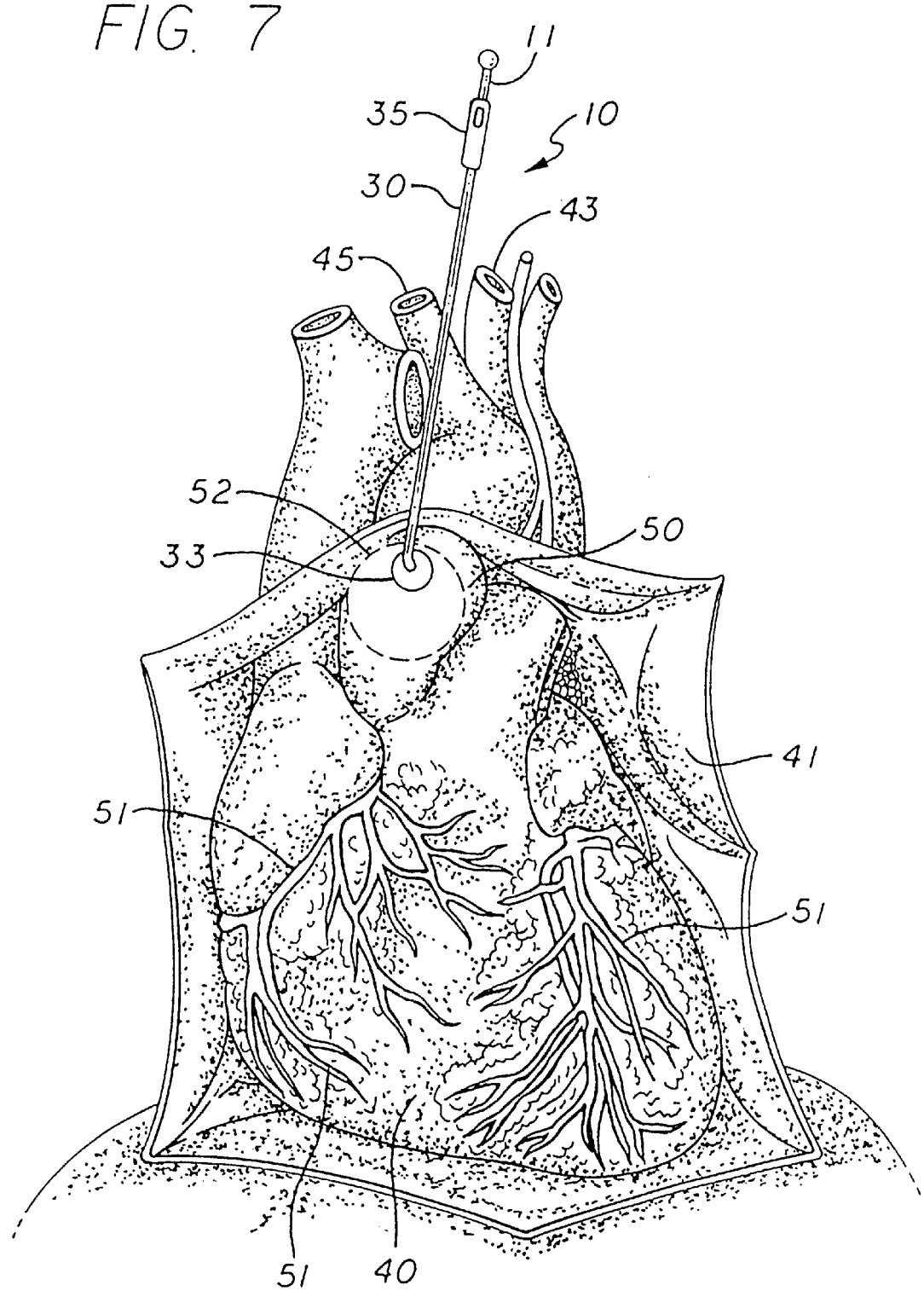

ENDOSCOPIC CARDIOPLEGIA INFUSION CANNULA AND METHOD OF USE

FIELD OF THE INVENTION

The invention relates generally to a cannula for infusing cardioplegic fluid into a body lumen. More specifically, the invention relates to a cannula, and a method of use, wherein the cannula is inserted through the thorax and into the ascending aorta, in a closed chest surgical procedure, and cardioplegic fluid is infused into the coronary arteries to arrest cardiac function.

BACKGROUND OF THE INVENTION

Various cardiovascular procedures have been performed for many years typically by opening the sternum (referred to as a median sternotomy), and connecting the patient to cardiopulmonary bypass equipment to maintain the circulation of oxygenated blood throughout the patient's circulatory system. In this manner, the heart can be stopped and various surgical procedures performed such as coronary artery bypass grafting and replacement of aortic, mitro and other heart valves. Numerous other surgical procedures have been performed in a similar manner.

As taught by conventional techniques, cardiopulmonary bypass is established by a venous cannula introduced into a major vein such as the inferior vena cava, or into the heart itself, to withdraw deoxygenated blood from the patient and route it to a cardiopulmonary bypass (CPB) machine for oxygenation. Generally, an arterial cannula is introduced into a major artery such as the aorta, or a femoral artery, to deliver oxygenated blood from the cardiopulmonary bypass machine to the patient's arterial system.

In surgical procedures where cardiac function is arrested, the heart and coronary arteries must be isolated from the patient's arterial system. Using conventional techniques, the sternum is cut longitudinally, referred to as a median sternotomy, to provide access to the heart and other thoracic vessels. One method taught in the prior art, is to mechanically cross-clamp the ascending aorta downstream of the ostia of the coronary arteries, but upstream of the brachiocephalic artery, which will allow oxygenated blood from the cardiopulmonary bypass machine to reach the arms, neck, head, and the remainder of the body. A catheter can then be introduced into the ascending aorta between the cross-clamp and the aortic valve. Cardioplegic fluid is then infused through the catheter and into the coronary arteries.

One particular prior art device currently under development and disclosed in the literature, includes partitioning the patient's ascending aorta between the coronary ostia and the brachiocephalic artery to isolate the heart and coronary arteries from the remainder of the arterial system, arresting cardiac function, and introducing a balloon catheter through a femoral or other artery. More particularly, all blood flow through the ascending aorta is blocked by an inflatable balloon disposed on the distal end of a catheter which has been introduced through the femoral artery. The expandable balloon is positioned in the ascending aorta between the coronary ostia and the brachiocephalic artery so that it will block substantially all blood flow therethrough. The device includes a port at the proximal end of the catheter shaft for delivering cardioplegic fluid into the patient's ascending aorta upstream of the occluding means.

For the purposes of the present application, "downstream" means in the direction of normal blood flow through a blood vessel, i.e., further from the heart in the arterial system, and closer to the heart in the venous system. "Upstream" means in the direction opposite of the downstream direction. References herein to the "proximal" direction, means in the direction toward the end of the device that is closest to and held or manipulated by the physician, while "distal" means in the direction away from the user, and opposite the proximal direction.

The prior art devices also disclose means for providing cardiopulmonary bypass systems in which a bypass cannula is introduced into an artery (typically the femoral artery), and a blood flow lumen in the bypass cannula is connected to a lumen for delivering oxygenated blood into the patient's arterial system. A bypass cannula also can be positioned in a vein in the patient, and the blood flow lumen in the bypass cannula is connected to a means for receiving deoxygenated blood from the patient's venous system.

Generally, with the prior art devices, the aorta occluding device, generally a catheter having an inflatable balloon, is typically introduced transluminally, generally from a femoral vein or artery and advanced intraluminally into the ascending aorta. Due to various reasons, it may not always be possible to insert a catheter into the femoral artery or veins, thus making this prior art technique sometimes difficult or impossible to perform.

Improved methods and devices are therefore necessary to establish CPB which will eliminate the need to introduce catheters or cannulas through the femoral veins or arteries for the purpose of occluding the ascending aorta and for infusing cardioplegic fluid. The present invention provides alternative devices and methods which will accomplish the desired surgical procedure without the attendant risks and problems associated with the conventional procedures described.

SUMMARY OF THE INVENTION

The present invention provides devices and methods for performing closed chest surgical procedures in which cardiac function is arrested and CPB is provided. The devices and methods of the present invention include an endoscopic cardioplegia infusion cannula for suprasternal insertion so that it may be advanced to and inserted in the ascending aorta.

Utilizing the present invention, all blood flow through the ascending aorta is blocked, and cardioplegic fluid is introduced and infused into the coronary arteries to arrest cardiac function. The patient is connected to a CPB system so that deoxygenated blood is removed from the patient, oxygenated, and returned to the patient. After cardiac function is arrested, any surgical procedure, such as coronary artery bypass, can be performed.

In a preferred embodiment, the present invention provides an infusion cannula for insertion into the ascending aorta, and an occlusion balloon is positioned at the distal end of the cannula for occluding the ascending aorta. An infusion port, upstream of the occlusion balloon, provides cardioplegia solution upstream of the occlusion balloon so that it may perfuse into the coronary arteries, while the occlusion balloon prevents any outflow of the cardioplegic fluid in the downstream direction.

The infusion cannula includes an outer sheath which is dimensioned for axial movement over the cannula body. The outer sheath has a flange at its distal end which is advanced into contact with the ascending aorta such that the outer wall of the ascending aorta is compressed between the flange and the occlusion balloon. Thus, a seal is created by the flange at the cannula entry point into the ascending aorta which is extremely important in a closed chest procedure. Leakage of blood flow where the cannula enters the ascending aorta in a closed chest procedure is far more difficult to correct than in an open chest procedure where there is easy access to the point of leakage.

In a closed chest procedure, there is limited space in the chest cavity, particularly above the heart where the majority of the surgical procedures will be performed. Accordingly, the invention provides for lifting the sternum to create a working space directly above the heart and the surrounding area. The cannula of the present invention has an angled bend at its distal end, preferably 90°, so that it can be more easily inserted into the ascending aorta. By lifting the sternum, a working space is created for the cannula and the angled bend at the distal end of the cannula. Further, a working space is created for other surgical instruments inserted percutaneously through intercostal penetrations.

According to the method of the invention, a pursestring suture is formed in the ascending aorta. The infusion cannula is introduced suprasternally (above the sternum) and the distal end of the cannula is positioned above the ascending aorta. An incision is performed in the ascending aorta approximately in the center of the pursestring suture previously placed. The distal end of the cannula is inserted into the ascending aorta and the occlusion balloon is inflated to completely block all of the blood flow through the aorta. The pursestring suture is drawn tightly around the cannula body to form a seal and prevent leakage of blood flow. The outer sheath is then advanced along the cannula until the flange of the outer sheath contacts the outside of the ascending aorta. The outer sheath is then locked so that there is no relative movement between the outer sheath and the cannula. The flange on the distal end of the outer sheath compresses the outer wall of the ascending aorta adjacent the occlusion balloon on the inside of the aorta, so that a fluid-tight seal is created at the point where the cannula is inserted into the aorta. Thereafter, cardioplegic solution is infused into the ascending aorta proximate to the occlusion balloon so that it can perfuse into the coronary arteries and arrest cardiac function. The patient is connected to a CPB machine to receive oxygenated blood, generally by a femoral bypass procedure.

Using the system and method of the present invention, the patient's cardiac function can be arrested and the patient placed on a cardiopulmonary bypass system so that various surgical procedures can be performed on the non-beating heart.

A further understanding of the scope and nature of the present invention is set forth in the remainder of the specification, claims, and drawings.

BRIEF DESCRIPTION OF THE DRAWINGS

FIG. 7 is an enlarged schematic view illustrating the cannula of the present invention inserted into the ascending aorta, and depicting the coronary arteries where cardioplegic solution is perfused in order to arrest cardiac function.

DETAILED DESCRIPTION OF THE PREFERRED EMBODIMENTS

With the advent of minimally invasive surgery there has developed a need for a device and its method of use for infusing cardioplegic solution into the heart and arresting cardiac function, so that closed chest surgical procedures can be performed. The present invention is particularly useful for use in conjunction with minimally invasive cardiac procedures such as repair or replacement of aortic, mitral, and other heart valves, repair of septal defects, pulmonary thrombectomy, electrophysiological mapping and ablation, coronary artery bypass grafting, angioplasty, atherectomy, and treating aneurysms, as well as neurovascular procedures. While the present invention is particularly useful in closed chest procedures, it also has the advantage of being used in open chest procedures where there are difficulties in accessing femoral or other arteries for intraluminal delivery of the occluding balloon.

Figure 1:
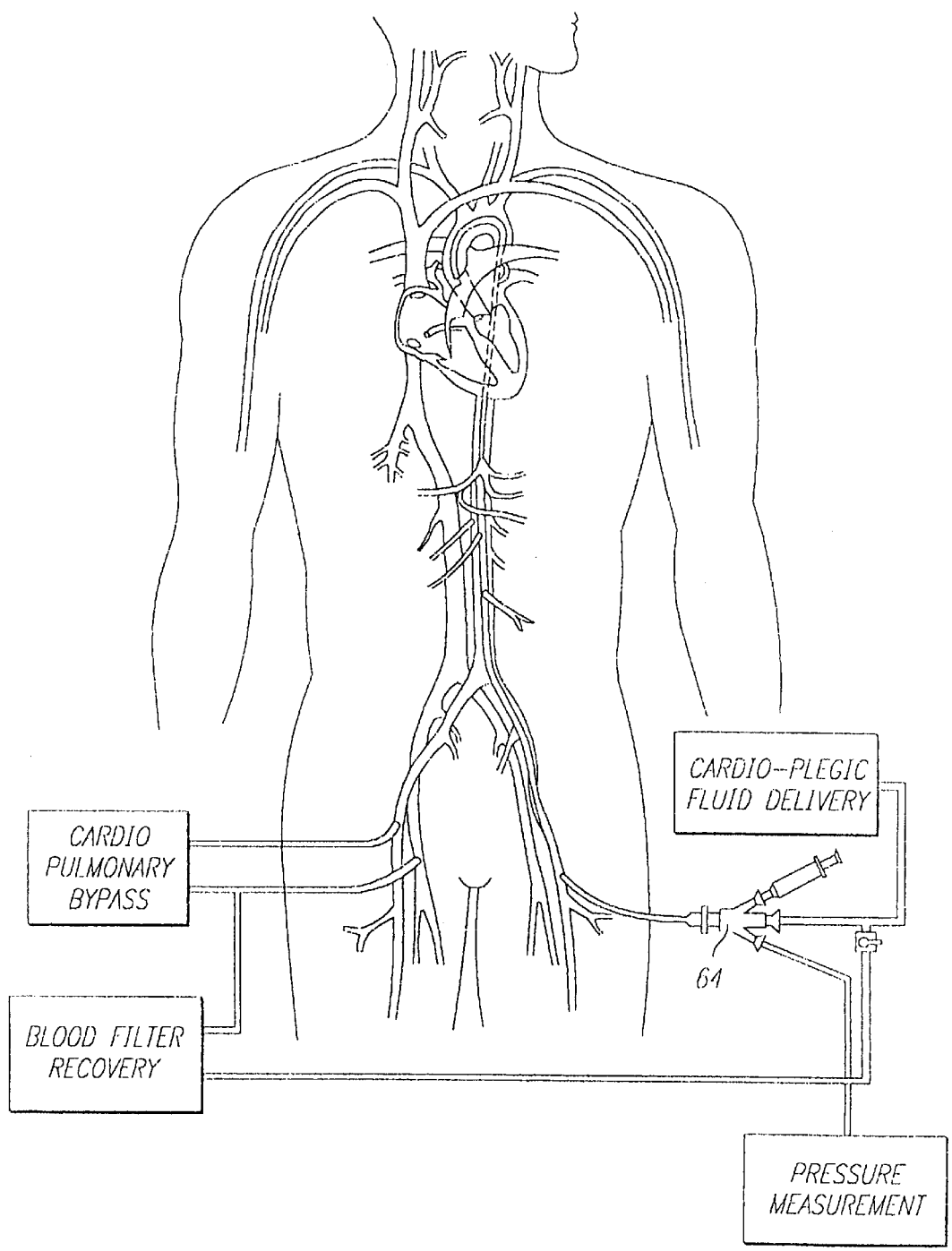
FIG. 1 is a schematic illustrating a prior art system for arresting cardiac function in which an occluding catheter is introduced through the femoral arteries and a cardiopulmonary bypass system is connected to the patient.
Figure 2:
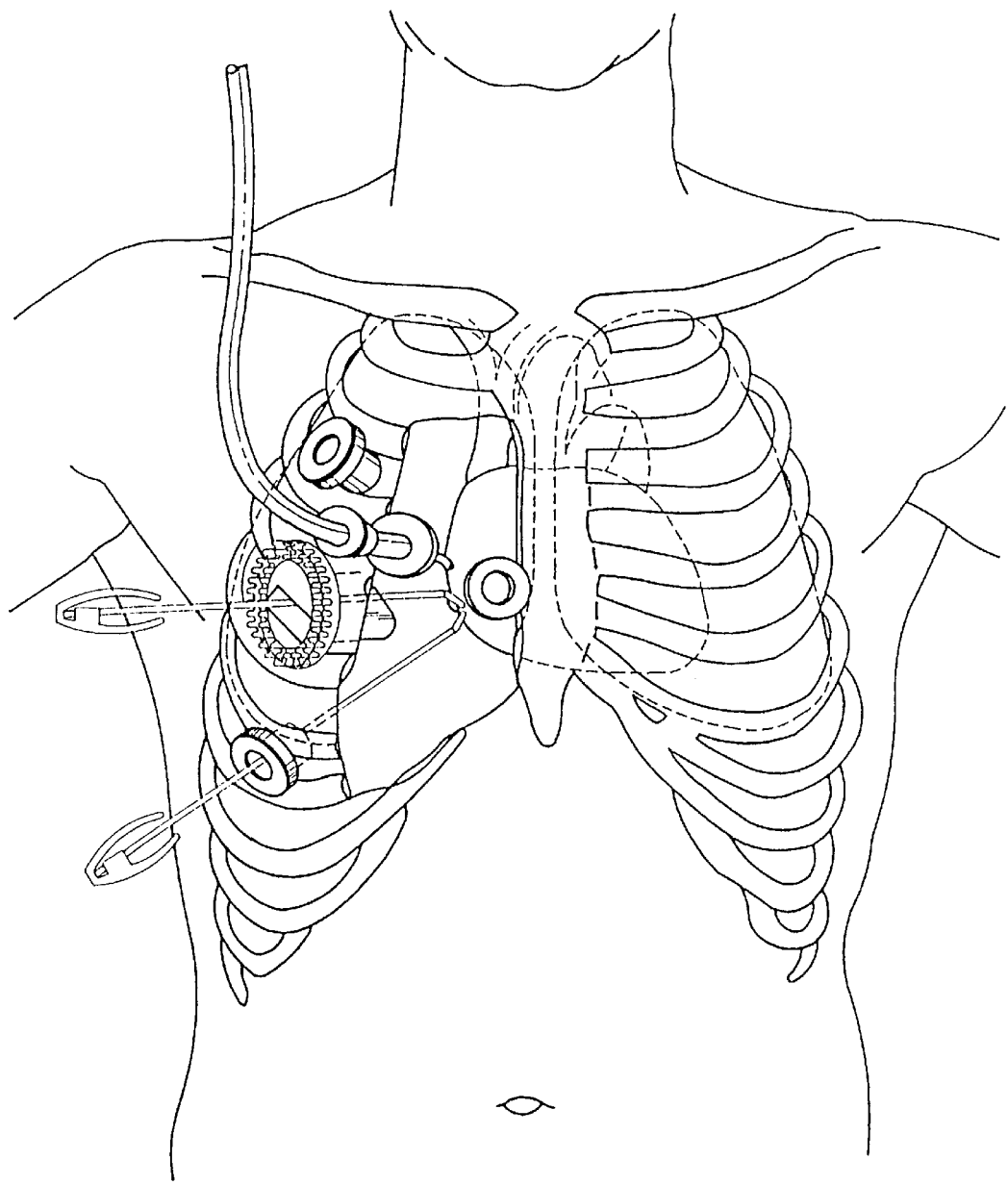
FIG. 2 is a schematic illustrating a system for performing a surgical procedure on a patient, wherein various surgical instruments are introduced through intercostal penetrations and viewed with an endoscope or similar device.

Turning to the drawing figures, FIGS. 1 and 2 depict prior art devices wherein a catheter is delivered intraluminally through a femoral access site and occludes the ascending aorta between the coronary ostia and the brachiocephalic artery. A cardiopulmonary bypass system is also introduced through the femoral or iliac arteries to remove deoxygenated blood and supply oxygenated blood to the patient. As depicted in FIG. 2, minimally invasive surgical instruments are introduced percutaneously through intercostal penetrations for use in surgical procedures in and on the heart. While the prior art devices as depicted in FIGS. 1 and 2 offer minimally invasive techniques, it may not be possible to access the femoral artery with an occlusion catheter and balloon to occlude the ascending aorta. Further, once three or four instruments, as depicted in FIG. 2, are inserted through intercostal penetrations, the operating area within the patient's chest cavity, and particularly above the heart, becomes crowded. Accordingly, there is a need for a device and method of use for infusing cardioplegic fluid in the ascending aorta, and separating the ascending aorta from the rest of the pulmonary system.

Figure 3:
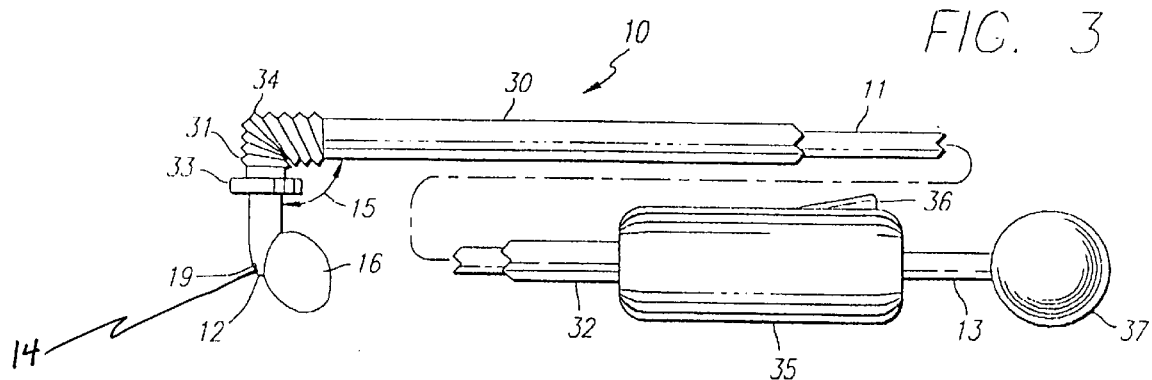
FIG. 3 is a side elevational view of the cannula of the present invention for use in partitioning the ascending aorta and infusing cardioplegic solution therein.
Figure 4:
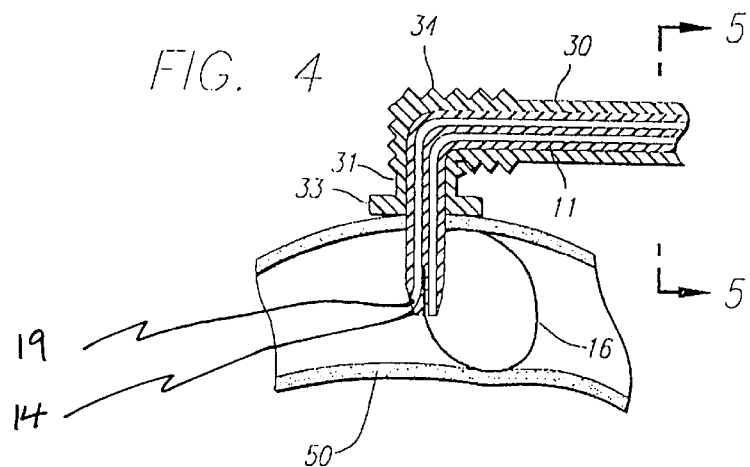
FIG. 4 is a partial cross-sectional view of the cannula of the present invention where the distal end has been inserted into a portion of the ascending aorta and an occlusion balloon has been expanded to completely block the aorta.
Figure 5:
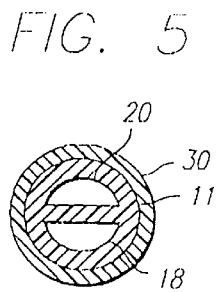
FIG. 5 is a cross-sectional view taken along lines 5—5 of FIG. 4, depicting the infusion lumen and inflation lumen of the cannula.
Figure 4A:
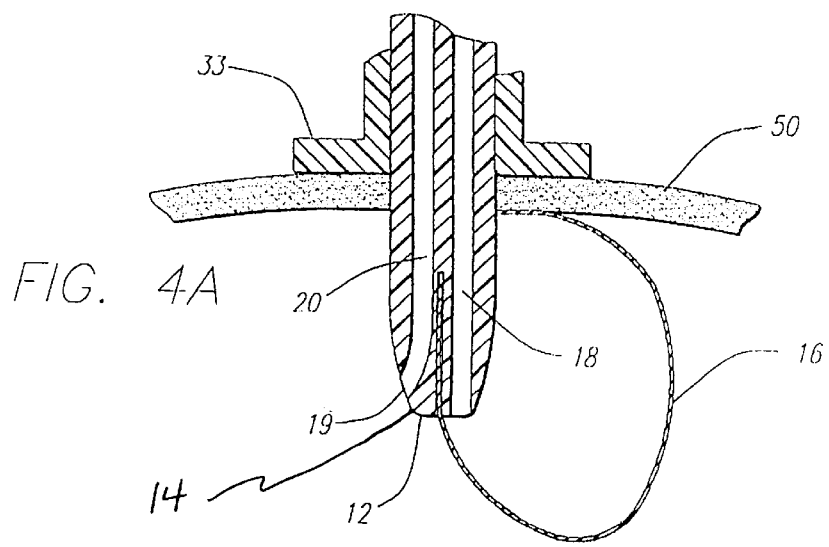
FIG. 4A is an enlarged partial cross-sectional view of the cannula of FIG. 4 depicting the infusion fluid lumen and the port for infusing cardioplegic solution into the aorta.

In a preferred embodiment, as depicted in FIGS. 3–5, the present invention includes a cannula 10 having an elongated cannula body 11 and a distal end 12 and a proximal end 13. Distal end 12 of elongated cannula body 11 has a tapered end 14 which facilitates insertion of the distal end 12 into the ascending aorta, as will be described. The cannula body 11 has a tapered end to facilitate insertion into the aorta. The inflation lumen 18 lies within the balloon 16. Outside of the balloon is another lumen 20, which infuses cardioplegic solution via port 19. The distal end of infusion lumen 20, together with the distal end of balloon inflation lumen 18, form a tapered tip. One wall of the balloon 16 lies between the balloon inflation lumen 18 and the infusion lumen 20.

These three elements may be bonded together at their adjoining surfaces to form a unitary tip, which may be easily inserted through a small incision. An angled bend 15 in elongated cannula body 11 provides precise positioning of distal end 12 when the cannula is inserted into the ascending aorta. An occlusion balloon 16 is attached near the distal end 12 of the elongated catheter body, and can be inflated from a collapsed state to completely occlude the ascending aorta. An inflation lumen 18, which extends through elongated cannula body 11, provides inflation fluid for occlusion balloon 16. A port 19 is formed in elongated cannula body 11 near distal end 12 for infusing cardioplegic solution proximate to occlusion balloon 16. An infusion lumen 20 is in fluid communication with port 19 and it extends through elongated cannula body 11. A conventional triple-arm adapter (not shown) can be connected to proximal end 13 of the elongated cannula body for infusion of inflation fluid and cardioplegic solution. An example of a typical triple-arm adapter is depicted in prior art FIG. 1.

In keeping with the preferred embodiment of the invention, elongated catheter body 11 is preferably formed of a polymeric material, such as a rigid plastic, which allows precise control over the distal end 12 as it is positioned over and inserted into the ascending aorta. Elongated catheter body 11 also can be formed of a metal alloy, such as stainless steel or titanium, or a combination of rigid plastic and a metal alloy. Further, since the cannula is designed to be rigid, it can be maneuvered without the need for a separate grasping instrument to hold and direct distal end 12 of cannula 10.

In order to facilitate placement of distal end 12 of cannula 10 in the ascending aorta, angled bend 15 is formed near the distal end of the cannula body. In the preferred embodiment, angled bend 15 is approximately 90° so that distal end 12 is approximately transverse to elongated catheter body 11. Preferably, angled bend 15 is between 20° and 150°, and most preferably it is approximately 90°. While it is preferred that elongated cannula body 11 be formed of a rigid plastic, and that angled bend 15 be fixed at the preferred angle, it is contemplated that angled bend 15 may be adjustable, depending upon the patient, the amount of space developed by sternal lifting, and any other factors which may determine more or less than the preferred 90° angulation.

The occlusion balloon 16 may be formed from an elastomeric material which is dimensioned to stretch and expand within the ascending aorta so that it completely blocks all blood flow.

As depicted in FIG. 5, elongated cannula body 11 is tubular and has so-called half-moon shaped inflation and infusion lumens 18,20. The tubular shape of the cannula and the specific shape of the lumens are by way of example and other shapes are contemplated. Cannula body 11 may have an eliptical shape and the lumens 18,20 might be circular, for example.

In keeping with the preferred embodiment, and as depicted in FIGS. 3–5, an outer sheath 30 is dimensioned for axial movement over elongated catheter body 11. Outer sheath 30 has a distal end 31 and a proximal end 32, and a flange or cuff 33 at its distal end. Outer sheath 30 is also formed of a substantially rigid plastic material and is dimensioned so that it slides over elongated catheter body 11, however, it is not a loose fit. At least a portion of outer sheath 30 has a plurality of pleats 34 near distal end 31 of outer sheath 30. The pleated end 34 is more flexible than the remainder of outer sheath 30, and is necessary to allow outer sheath 30 to be advanced over angled bend 15, as will be described herein. A handle 35 is attached to proximal end 32 of outer sheath 30 so that the physician may grip the handle and advance or retract outer sheath 30 along or over elongated cannula body 11. A locking means 36, which can include a locking lever or button mounted on handle 35, allows the physician to lock outer sheath 30 against elongated cannula body 11 so that there is no relative movement therebetween. A knob 37 is provided on proximal end 13 of elongated catheter body 11 so that the physician can more easily manipulate and control elongated cannula body 11 as it is being inserted into the patient.

Figure 6:
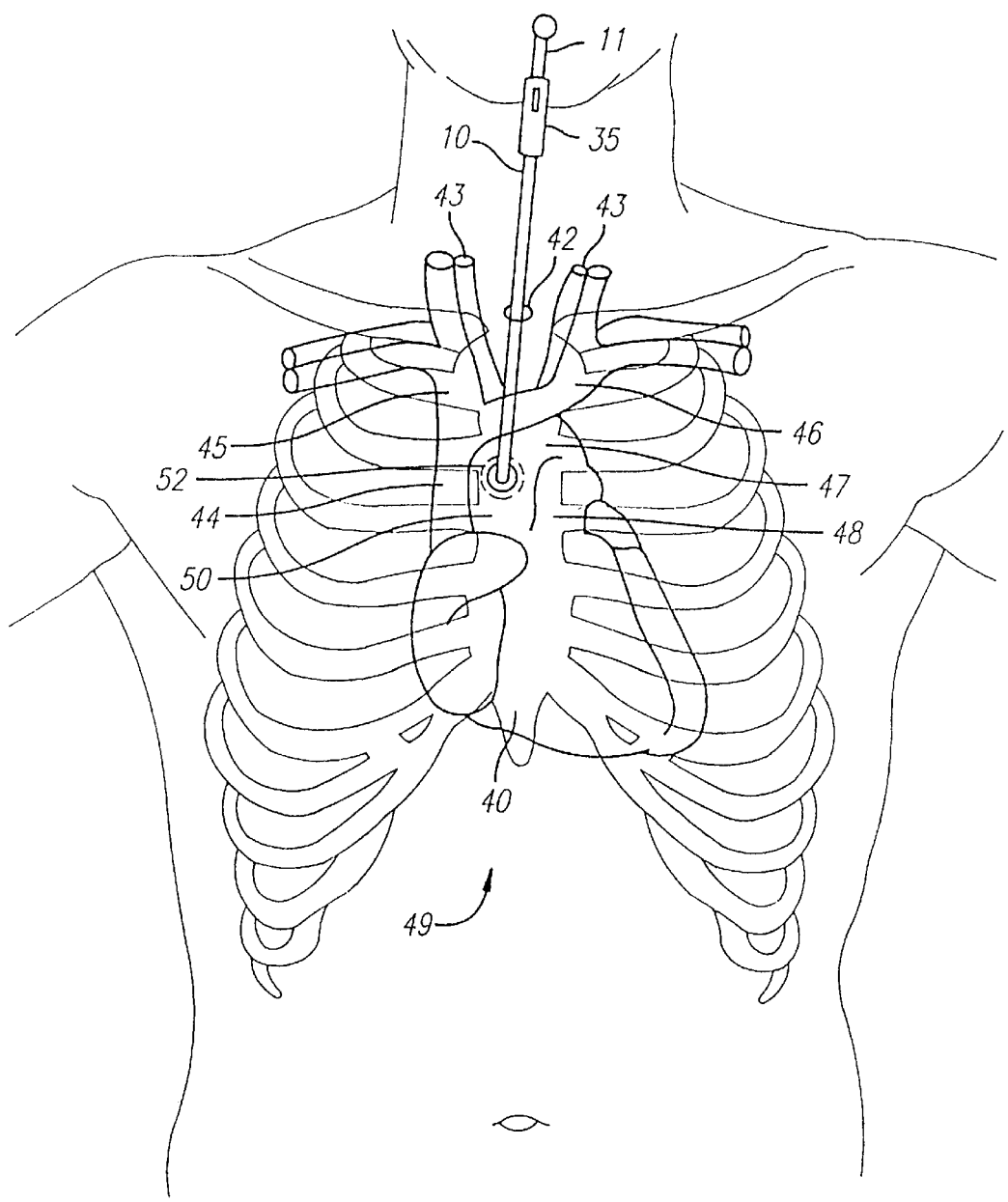
FIG. 6 schematically illustrates the cannula of the present invention introduced suprasternally and depicting the distal end of the cannula inserted into the ascending aorta.

Referring now to FIGS. 6 and 7, the method of using the devices of FIGS. 3–5 will be described. It is to be understood that the preferred method of use of the present invention is to be performed in a closed chest environment, however, the present invention also would be useful in an open chest procedure.

With this in mind, and with reference to FIGS. 6 and 7, a brief discussion of the anatomy is appropriate for a clearer understanding of the use of the present invention. As is depicted heart 40 is surrounded by pericardium 41 which generally must be incised and pulled back for access to the heart tissue, valves, and various arteries. The cannula of the present invention is dimensioned for suprasternal insertion in throat area 42. The common carotid arteries 43, superior vena cava 44, and right and left brachiocephalic veins 45,46 respectively, are upstream of ascending aorta 50. The sternum, which is generally located at arrow 49, is to be lifted by known methods in order to create a working space above heart 40. As will be described, one of the primary purposes for occluding the ascending aorta is to perfuse cardioplegic fluid into coronary arteries 51.

In a preferred method of practicing the invention, a working space is obtained over heart 40 by sternal lifting which is well known. Since ascending aorta 50 is contained within the pericardial sac, pericardium 41 must be incised and drawn aside so that access to ascending aorta 50 is provided. A pursestring suture 52 is placed in ascending aorta 50 by known methods. An incision is placed in the neck area 42 and cannula 10 is inserted therethrough. Since cannula 10 is preferably formed from a rigid plastic, precise control over distal end 12 is obtained without the need for grasping tools. Distal end 12 of elongated catheter body 11 is positioned over the ascending aorta by manipulating and advancing elongated cannula body 11. An incision is made in the center of pursestring suture 52 and distal end 12 of elongated cannula body 11 is inserted into ascending aorta 50 through the incision. Tapered distal end 14 in the cannula body facilitates insertion of the distal end of the cannula into the ascending aorta. Once the tapered distal end 14 is inserted into the ascending aorta, pursestring suture 52 is drawn tight around elongated cannula body 11 to further prevent leaks, and occlusion balloon 16 is immediately inflated to completely block all blood flow in ascending aorta 50, which will also reduce leakage at the point where the cannula was inserted into the aorta.

In further keeping with the method of the present invention, outer sheath 30 is advanced distally until flange 33 contacts the outer surface of ascending aorta 50. As outer sheath 30 is advanced, flexible pleats 34 and flange 33 slide over the angled bend 15 of the cannula body. A further seal is created by flange 33 compressing the outer wall of ascending aorta 50, while occlusion balloon 16 presses against the inner wall of the ascending aorta. Thus, the compressive forces effectively prevent leaks which are difficult to correct in a closed chest environment. As will be appreciated, flange 33 must be stiff enough to create a seal, yet not so rigid that it damages the ascending aorta. Thus, it is preferred that flange 33 be made from an open cell foam that is firm, but will not damage the outer surface of the aorta. In order to insure that flange 33 continues to press on ascending aorta 50 and form a seal, outer sheath 30 is locked in position relative to elongated catheter 11 by depressing locking means 36, which can include a conventional locking lever or button.

In keeping with the preferred method, cardioplegic solution is provided via infusion lumen 20 so that it exits port 19 which is proximate (upstream) of occlusion balloon 16. The cardioplegic solution infuses into the coronary arteries 51 as is depicted in FIG. 7. Shortly after the cardioplegic solution is infused into coronary arteries 51, cardiac activity should cease and heart 40 should remain substantially immobile while the physician performs a surgical procedure.

As is well known in the art, cardiopulmonary bypass is simultaneously provided with the method of the present invention so that oxygenated blood is continuously supplied to the patient.

One advantage to the present invention over the prior art devices is to insert cannula 10 suprasternally so that proximal end 13 of elongated cannula body 11, remains near the patient's head and away from any instruments introduced intercostally. For example, the prior art devices depicted in FIG. 2 disclose surgical instruments, viewing scopes, and the like, which are introduced percutaneously through intercostal penetrations. All of the instruments are crowded around and above the heart area where space is limited. Thus, suprasternal insertion of the cannula of the present invention allows the cannula to be clear of the other instruments. The prior art instruments are close together and to insert the cannula of the present invention through an intercostal penetration would further congest the area. Moreover, as previously described, an occluding catheter such as that described in the prior art may be too large for transluminal delivery through the femoral arteries.

While the invention and its method of use has been described herein, it will be clear to those skilled in the art that the cannula and its method of insertion can be used in other vessels in the heart. Further, materials and dimensions disclosed herein are intended by way of illustration only, and are not meant to limit the scope of the invention. Accordingly, other modifications and improvements may be made without departing from the scope and nature of the present invention.

What is claimed is:

1. A method of inserting a cannula into the ascending aorta and infusing cardioplegic solution therein, the cannula having an elongated cannula body with an angled bend formed in a distal end thereof, an occlusion balloon positioned at the distal end of the elongated cannula body, and an outer sheath surrounding the elongated cannula body and dimensioned for axial movement there along, the method comprising:

inserting the elongated cannula body into a body cavity;
 positioning the distal end of the elongated cannula body over the ascending aorta;
 incising the aorta in the center of a pursestring suture previously formed in the ascending aorta;
 inserting the distal end of the elongated cannula body into the ascending aorta and inflating the occlusion balloon therein;
 drawing the pursestring suture around the elongated cannula body;
 advancing the outer sheath until the distal end thereof is in contact with the ascending aorta thereby compressing a portion of the ascending aorta between the distal end of the outer sheath and the occlusion balloon; and
 infusing a cardioplegic solution into the ascending aorta proximate to the occlusion balloon so that the cardioplegic solution perfuses into the coronary arteries.

2. The method of claim 1, wherein the sternum is lifted to create space above the ascending aorta.

3. The method of claim 2, wherein the sternum is lifted to create a working space over the heart and the ascending aorta.

4. The method of claim 1, wherein the outer sheath includes a flange at its distal end, the method further comprising advancing the outer sheath so that a portion of the ascending aorta is compressed between the flange contacting the outside of the ascending aorta and the occlusion balloon contacting the inside of the ascending aorta.

5. The method of claim 4, wherein the outer sheath is locked with respect to elongated cannula body so that the flange remains in contact with the outside of the ascending aorta thereby providing a seal where the cannula body enters the ascending aorta.

6. The method of claim 1, wherein the occlusion balloon is deflated after a medical procedure is performed.

7. The method of claim 6, wherein the elongated cannula body is removed from the ascending aorta and the incision is closed by drawing and tying the pursestring suture.

8. The method of claim 1, wherein the cannula is inserted suprasternally.

9. A method of closed-chest cannulation of the ascending aorta and infusing cardioplegic solution therein, including a cannula having an elongated cannula body with an angled bend formed in a distal end thereof, an occlusion balloon positioned at the distal end of the elongate cannula body, and an outer sheath surrounding the elongated cannula body and dimensioned for axial movement therealong, the method comprising:

lifting the sternum to create a space above the heart area;
 providing a pursestring suture in the ascending aorta;
 suprasternal insertion of the elongated cannula body and positioning the distal end of the cannula body above the ascending aorta;
 incising the ascending aorta in the center of the pursestring suture;
 inserting the distal end of the elongated cannula body into the ascending aorta;
 drawing the pursestring suture around the elongated cannula body to create a seal and prevent leakage;
 inflating the occlusion balloon in the ascending aorta;
 advancing the outer sheath, which has a flange on its distal end, so that the flange is in contact with the outside of the ascending aorta, thereby compressing the ascending aorta between the flange and the occlusion balloon; and
 infusing a cardioplegic solution into the ascending aorta proximate to the occlusion balloon so that the cardioplegic solution perfuses into the coronary arteries.

10. The method of claim 9, wherein the outer sheath is locked with respect to the elongated cannula body so that the flange remains in contact with the outside of the ascending aorta thereby providing a seal where the distal end of the cannula body enters the ascending aorta.

11. The method of claim 9, wherein the occlusion balloon is deflated after a medical procedure is performed.

12. The method of claim 9, wherein the elongated cannula body is removed from the ascending aorta and the incision is closed by drawing and tying the pursestring suture.

13. A cannula for insertion into the ascending aorta, comprising:

an elongated cannula body having a distal end and a proximal end;

an angled bend formed in the distal end of the elongated cannula body;

an occlusion balloon positioned at the distal end of the elongated cannula body; and a sheath having a sufficiently flexible distal end for facilitating movement around an angle of varying degrees, a proximal end, and dimensioned to slidably advance and retract over the elongated cannula body so that when the distal end of the elongated cannula body is inserted into the ascending aorta the sheath can be advanced distally until a portion of the ascending aorta is positioned between the occlusion balloon and the distal end of the sheath.

14. The cannula of claim 13, wherein the occlusion balloon is dimensioned to occlude the ascending aorta.

15. The cannula of claim 9, wherein the occlusion balloon is formed from an elastomeric material.

16. The cannula of claim 13, wherein the elongated cannula body includes a port near the distal end of the elongated cannula body and an infusion lumen in fluid communication with the port for infusing cardioplegic solution upstream of the occlusion balloon and into the coronary arteries.

17. The cannula of claim 16, wherein the port is positioned proximate to the occlusion balloon so that after the occlusion balloon is inflated, cardioplegic solution is infused into the coronary arteries and the expanded balloon prevents the cardioplegic solution from entering the brachiocephalic and carotid arteries.

18. The cannula of claim 13, wherein the angled bend is an approximately 90° bend relative to the elongated cannula body.

19. The cannula of claim 13, wherein the angled bend is in the range of 20° to 150° relative to the elongated cannula body.

20. The cannula of claim 13, wherein the elongated cannula body is formed from a rigid plastic.

21. The cannula of claim 13, wherein the elongated cannula body is formed from a metallic alloy taken from the group of metallic alloys including stainless steel and titantium.

22. The cannula of claim 13, wherein at least a portion of the elongated cannula body is formed from a polymeric material.

23. The cannula of claim 13, wherein the distal end of the elongated cannula body is tapered to facilitate entry of the cannula into the ascending aorta.

24. The cannula of claim 13, wherein the elongated cannula body is dimensioned for suprasternal insertion and extending to the ascending aorta.

25. The cannula of claim 13, wherein the elongated cannula body includes an inflation lumen for inflating the occlusion balloon.

26. A cannula for insertion into the ascending aorta, comprising:

an elongated cannula body having a distal end and a proximal end;

an angled bend formed in the distal end of the elongated cannula body;

an expandable member on the distal end of the elongated cannula body for occluding the ascending aorta; and an outer sheath disposed over a portion of the elongated cannula body and dimensioned for sliding movement over the elongated cannula body, the outer sheath having a sufficiently flexible distal end for facilitating movement around an angle of varying degrees, a proximal end and a flange on the distal end so that when the distal end of the elongated cannula body is inserted into the ascending aorta, the outer sheath can be advanced until a portion of the ascending aorta is positioned between the expandable member and the flange on the outer sheath.

27. The cannula of claim 26, wherein the elongated cannula body includes a port near the distal end of the elongated cannula body and an infusion lumen in fluid communication with the port for infusing cardioplegic solution through the port and into the coronary arteries.

28. The cannula of claim 27, wherein the port is positioned proximate to the expandable member so that after the expandable member is inflated, cardioplegic solution is infused into the coronary arteries, the expandable member thereby preventing the cardioplegic solution from entering the brachiocephalic and carotid arteries.

29. The cannula of claim 26, wherein the angled bend is an approximately 90° bend relative to the elongated cannula body.

30. The cannula of claim 26, wherein the angled bend is in the range of 20° to 150° relative to the elongated cannula body.

31. The cannula of claim 26, wherein the distal end of the elongated cannula body is tapered to facilitate entry of the cannula into the ascending aorta.

32. The cannula of claim 26, wherein the elongated cannula body is dimensioned for suprasternal insertion and extending to the ascending aorta.

33. The cannula of claim 26, wherein the expandable member is an occlusion balloon dimensioned to occlude the ascending aorta.

34. The cannula of claim 33, wherein is formed from an elastomeric material.

35. The cannula of claim 26, wherein the elongated cannula body includes an inflation lumen for inflating the expandable member.

36. The cannula of claim 26, wherein the flange on the distal end of the outer sheath is formed from open cell plastic foam.

37. The cannula of claim 26, wherein at least a portion of the distal end of the outer sheath includes a plurality of pleats which facilitate bending of the outer sheath as it advances over the angled bend in the elongated cannula body.

* * * * *

UNITED STATES PATENT AND TRADEMARK OFFICE
CERTIFICATE OF CORRECTION

PATENT NO. : 5,980,503
DATED : Nov. 9, 1999
INVENTOR(S) : Albert K. Chin

It is certified that error appears in the above-identified patent and that said Letters Patent is hereby corrected as shown below:

Column 9, line 21, claim 15, change "9", to read --14--.

Column 10, line 46, claim 34, after "wherein", add --the occlusion balloon--.

Signed and Sealed this

Ninth Day of May, 2000

Attest:

Q. TODD DICKINSON

*Attesting Officer*      *Director of Patents and Trademarks*